United States Patent [19]
Ferrari

[11] Patent Number: 5,571,165
[45] Date of Patent: Nov. 5, 1996

[54] X-RAY TRANSMISSIVE TRANSCUTANEOUS STIMULATING ELECTRODE

[76] Inventor: R. Keith Ferrari, 6525 Radcliff Dr., Nashville, Tenn. 37221

[21] Appl. No.: 569,567

[22] Filed: Dec. 8, 1995

[51] Int. Cl.$^6$ .............................. A61N 1/04; A61B 5/04
[52] U.S. Cl. ............................................. 607/142; 607/152
[58] Field of Search ..................................... 607/142, 149, 607/152; 128/639, 640; 602/153

[56] References Cited

U.S. PATENT DOCUMENTS

| | | |
|---|---|---|
| 4,050,453 | 9/1977 | Castillo et al. . |
| 4,226,247 | 10/1980 | Hauser et al. . |
| 4,239,046 | 12/1980 | Ong . |
| 4,257,424 | 3/1981 | Cartmell . |
| 4,370,984 | 2/1983 | Cartmell . |
| 4,422,461 | 12/1983 | Glumac ................................. 607/152 |
| 4,442,315 | 4/1984 | Segawa . |
| 4,539,995 | 9/1985 | Segawa . |
| 4,722,354 | 2/1988 | Axelgaard et al. . |
| 4,748,983 | 5/1988 | Shigeta et al. . |
| 4,800,887 | 1/1989 | Shigeta et al. . |
| 4,852,571 | 8/1989 | Gadsby et al. ......................... 128/640 |
| 4,852,585 | 8/1989 | Heath . |
| 4,895,169 | 1/1990 | Heath . |
| 5,265,579 | 11/1993 | Ferrari . |
| 5,330,526 | 7/1994 | Fincke et al. . |
| 5,356,428 | 10/1994 | Way . |
| 5,366,497 | 11/1994 | Ilvento et al. . |
| 5,431,166 | 7/1995 | Macur ..................................... 607/149 |

*Primary Examiner*—William E. Kamm
*Assistant Examiner*—George R. Evanisko
*Attorney, Agent, or Firm*—Vernon J. Pillote

[57] ABSTRACT

A disposable transcutaneous electrode comprising, a sheet electrode member of electrically conductive carbon filled polymer, an electrically conductive silver/silver chloride coating on at least a major portion of the lower side of the electrode member, a pad of electrically conductive gel having an upper surface underlying the silver/silver chloride coating on the lower side of the electrode member, a current distributing mat having a perimeter spaced inwardly of the perimeter of the electrode member, the mat including an open mesh metallized carbon fiber web having a carbon impregnated pressure sensitive adhesive composition on upper and lower sides of the web, the mat being configured to be electrically conductive along the surfaces of the mat and transverse to the surfaces of the mat and being conductively adhered to the upper side of the sheet electrode member, an electrical conductor sheathed in an electrical insulating material and having an unsheathed end portion conductively adhered to the mat for conducting defibrillating energy to or from the upper side of the mat, the sheet electrode member and the current distributing mat being configured to be X-ray transparent and capable of conducting energy at levels sufficient for defibrillation.

25 Claims, 2 Drawing Sheets

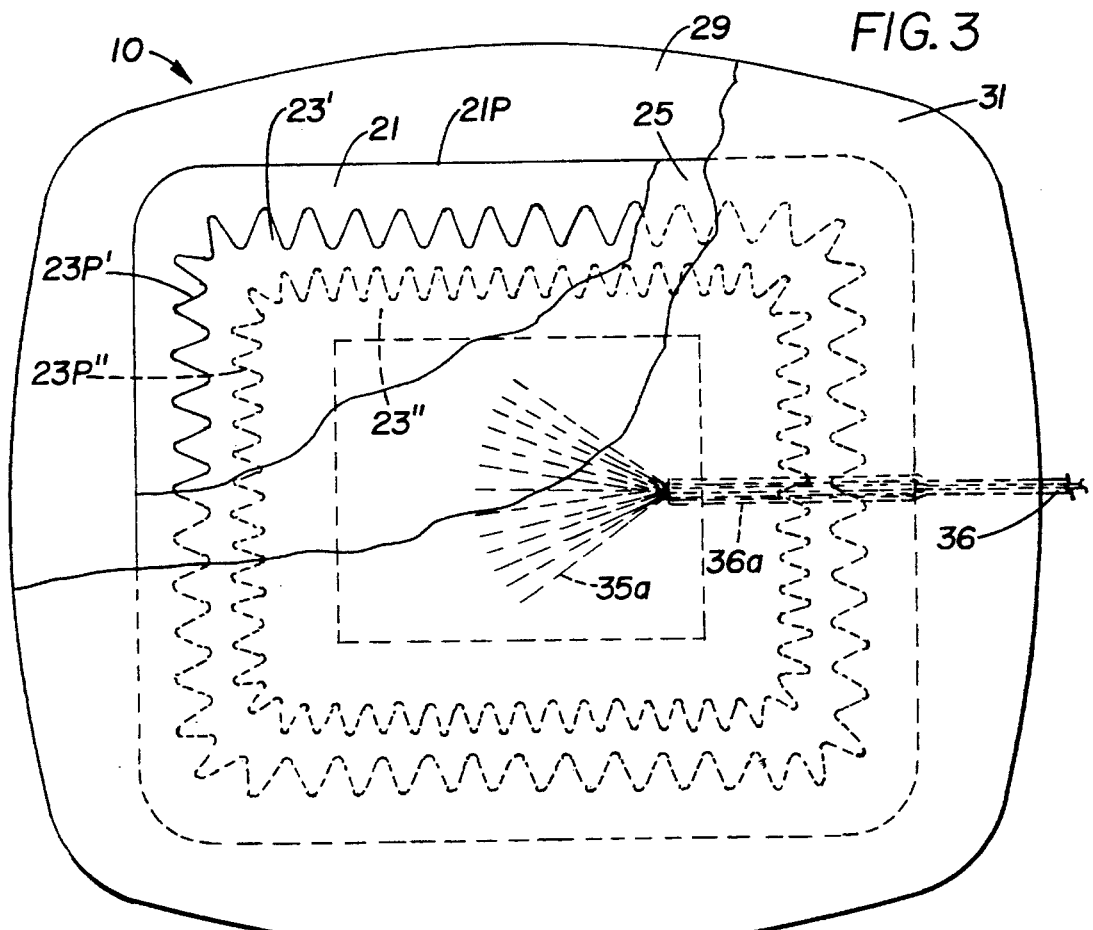
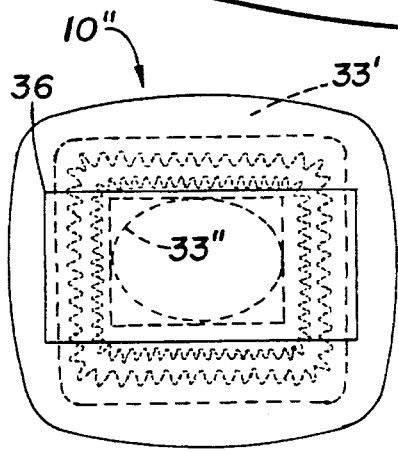
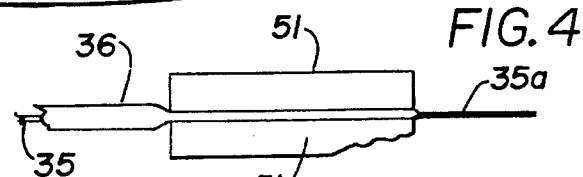
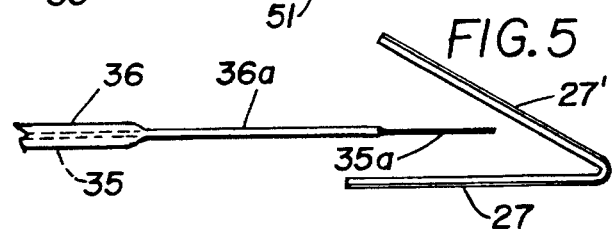
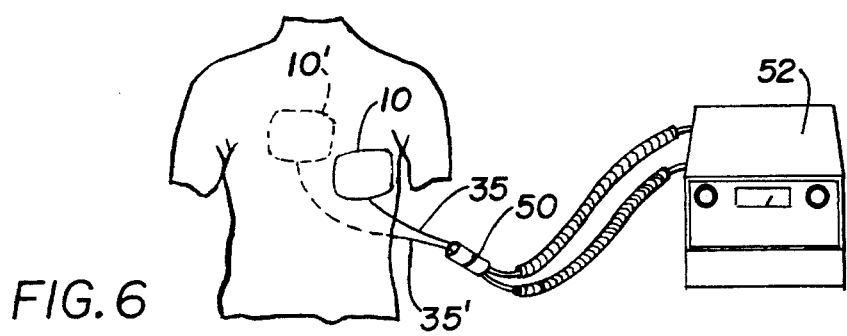

5,571,165

X-RAY TRANSMISSIVE TRANSCUTANEOUS STIMULATING ELECTRODE

BACKGROUND OF THE INVENTION

Various X-ray transmissive monitoring electrodes have heretofore been made to facilitate X-ray examination of a patient without requiring removal of the electrodes or significantly impairing the X-ray image. Examples of X-ray transmissive monitoring electrodes are disclosed in U.S. Pat. Nos. 4,050,453; 4,257,424; 4,370,984; 4,674,511; 4,685,467; 4,442,315; 4,539,995; and 5,265,579. Monitoring electrodes are very small, for example in the order of a few square centimeters and need only carry very low electrical signals in the order of milliamps. In general, such X-ray transmissive monitoring electrodes are not capable of conducting and distributing the high levels of energy required in transcutaneous stimulation and defibrillation electrodes.

Defibrillation electrodes must be capable of conducting the high energy level required for defibrillation, up to 360 Joules or more and must also distribute the energy over a relatively large area of the patient's epidermis to achieve adequate current density distribution within the ventricles. The ANSI/AAMI presently specify that the minimum active area of individual self-adhesive electrodes used for adult defibrillation and pacing shall be at least 50 square centimeters and that the total area of the two electrodes shall be at least 150 square centimeters.

Some prior defibrillation electrodes such as disclosed in U.S. Pat. Nos. 4,895,169 and 5,330,526, provide an electrically conductive metal plate having an area to substantially cover the skin contacting gel pad, for distributing the energy over the area of the pad. U.S. Pat. No. 4,748,983 provides an electrode body formed of a porous granular or fibrous carbon impregnated with an electrolytic solution that covers the upper surface of a skin contacting gel pad. Some other stimulation and defibrillation electrodes disclosed in U.S. Pat. Nos. 4,226,247; 4,239,046; 4,722,354; 5,356,428 and 5,366,497 provide a conductive backing for covering the skin contacting pad and which is formed of expanded metal or metal strands that are woven or formed into an open mesh.

Some of the above patents indicate that the backing is radiolucent or have at least some degree of X-ray transmissivity. In addition, some of the above patents also indicate that the defibrillation electrode disclosed in the patents are combination electrodes that can also function as monitoring electrodes between defibrillation pulses. However, it remains a problem to improve the X-ray transparency of defibrillation electrodes and the ability of the defibrillation electrodes to reliably function as monitoring electrodes promptly after transmission of a defibrillation pulse through the electrode. In addition, problems have been encountered with prior art stimulation and defibrillator electrodes, particularly after application of repeated high level defibrillation or cardiac pacing pulses, with irritation and burning of the patient's skin due to high current density around the perimeter of electrodes.

SUMMARY OF THE INVENTION

It is an object of the present invention to provide a disposable transcutaneous electrode which is X-ray transparent and capable of conducting energy sufficient for defibrillation, and which has improved current density distribution between the electrode and the skin surface of the patient to efficiently deliver the energy without burning the patient's skin.

Accordingly, the present invention provides a transcutaneous stimulation electrode comprising a sheet electrode member of electrically conductive carbon filled polymer having an electrically conductive silver/silver chloride coating on a lower side of the electrode member, a pad of electrically conductive gel underlying the electrode members and a current distributing mat on the upper surface of the electrode member. The current distributing mat includes an open mesh metallized carbon fiber web having a carbon impregnated pressure sensitive adhesive composition on the upper and lower sides of the web and which is configured to be electrically conductive along the surface of the mat and transverse to the surface of the mat to transfer and distribute energy between the upper surface of the mat and the upper surface of the sheet electrode member. The sheet electrode member is electrically conductive and transmits energy from the upper surface to the silver/silver chloride coating on the under surface. The sheet electrode member has an area sufficiently large to achieve adequate current density distribution between the electrode and the skin of the patient and the conductive mat has an area smaller than the area of the electrode member but large enough to distribute the current over an area on the upper side of the electrode. The silver/silver chloride coating on the under side of the electrode is advantageously arranged to have an outer perimeter that is spaced inwardly of the outer perimeter of the electrode member to reduce the current density at the outer perimeter of the electrode member.

Electrical energy is conducted to or from the upper surface of the conductive mat and a medical device. For applications in which radio translucency of the conductors is not essential, the conductors can be multi-strand metal wires in which the strands can be spread out and bonded to the upper surface of the mat. In applications where radio translucency of the wires is also important, the wires are advantageously formed of an X-ray transparent metal coated carbon fiber tow. It is also contemplated that the electrodes can be used as pad electrodes in which hand held defibrillation paddles are used to transfer current to or from the upper side of the conductor mat.

BRIEF DESCRIPTION OF THE DRAWINGS

FIG. 3 is a bottom plan view of the electrode, with certain layers broken away to illustrate the under side of intermediate layers;

FIG. 4 is a fragmentary sectional view through heated sealing jaws, illustrating flattening of the electric insulation adjacent the end of the conductors;

FIG. 5 is a diagrammatic view illustrating assembly of the conductor between layers of a electrically conductive mat;

FIG. 6 is a diagrammatic view illustrating application of the electrodes to a patient and connection to a defibrillating and ECG apparatus.

FIG. 7 is a top plan view of an electrode modified for use with defibrillating paddles, on a smaller scale than FIGS. 1 and 3; and

DETAILED DESCRIPTION

Figure 2:
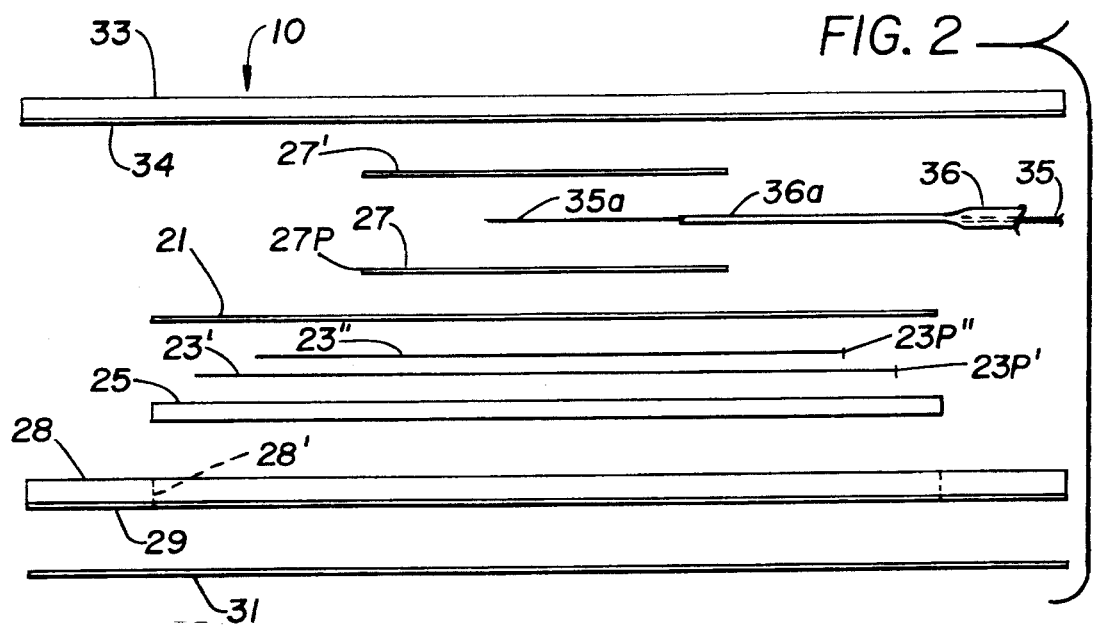
FIG. 2 is an exploded longitudinal sectional view of the electrodes.

An exploded view of a disposable transcutaneous electrode 10 embodying the present invention is illustrated in FIG. 2. In general, the electrode comprises a sheet electrode member 21 of electrically conductive carbon filled polymer; an electrically conductive silver/silver chloride coating 23 on at least a major portion of the lower side of the electrode member; a pad of electrically conductive gel 25 underlying the silver/silver chloride coating on the lower side of the electrode member, and a current distributing mat 27 having a lower surface conductively adhered to the upper side of the sheet electrode member, for conducting energy to or from the upper side of the electrode member. The electrode is configured to be X-ray transparent and capable of conducting electrical energy at levels sufficient for defibrillation. As used herein the phrase "X-ray transparent" is defined as the quality of being at least substantially invisible at X-irradiation levels used in routine X-rays of a patient's chest.

The gel pad 25 is preferably a skin compatible hydrogel having good ability to retain moisture content and adhesive tack. The gel may, for example, comprise a hydrogel marketed by Ludlow Technical Products division of Ludlow Corporation, under the trademark "Promeon", product number RG73P. It is desirable to laterally confine the gel pad 25 during storage and use, and the gel pad is preferably disposed within an opening 28' in a base frame 28 of X-ray transparent and electrically insulative foam such as 0.08 to 0.16 cm thick PE foam, and a removable release carrier sheet 31, for example of PTFE, is attached to the underside of the base frame 28 by a skin compatible adhesive coating 29 on the underside of the base frame. The carrier sheet underlies the gel pad 25 and covers the latter prior to use. An electrically insulative cover sheet 33 of X-ray transparent and electrically insulative foam such as 0.08 cm to 0.16 cm thick PE foam having an adhesive layer 34, overlies the current distributing mat 27 and the electrode member 21 and is adhered by the adhesive layer 34 to the upper side of the base frame 28. The gel pad 25 is of a type that adhesively connects the electrode member to the patient's skin and the adhesive 29 on the underside of the base frame 28 aids in adhering the electrode member to the patient's skin during use. Alternatively, the frame 28 could be omitted and the adhesive layer on the outer periphery of the cover sheet 33 used to adhere the electrode to the patient's skin.

Means are provided for conducting energy to and from the upper side of the current distributing mat 27 and a medical device. In the embodiment illustrated in FIGS. 1–6, the energy conducting means comprises an electrical conductor 35 having an electrically insulative sheath 36a and a unsheathed end portion 35a that is conductively adhered to the upper side of the current distributing mat 27. The current distributing mat preferably includes a second mat portion 27' arranged to overlie the mat 27 and the unsheathed end portion 35a of the conductor 35.

The electrode member 21 is formed of a thin flexible sheet of electrically conductive polymer film such as graphite filled polyvinyl chloride film preferably having a thickness of the order of two to four mils. An example of carbon filled polymer which can be used is thin carbon filled PVC available from Burkhardt/Freeman, Holyoke, Mass., under the trademark "Conducton".

The carbon filled sheet electrode member is X-ray transparent and the coating 23 of silver/silver chloride is applied in a layer or layers to the lower face of the electrode member as by silk screening or by flexographic printing. The silver/silver chloride coating is preferably less than ten microns in thickness, sufficient to provide good electrical conductivity without impairing the X-ray transparency of the electrode member. A carbon filled PVC material with silver/silver chloride coating on the underside suitable for use as an electrode member is available from Prime Label And Screen, Inc., New Berlin, Wis.

The electrode member 21 has a surface area dimensioned to distribute energy over an area of the patient's epidermis to achieve proper current density distribution within the ventricles of the patient's heart. The ANSI standards for the size of defibrillation electrodes published by AAMI presently recommends that the minimum active area of individual self-adhesive electrodes used for adult defibrillation and pacing shall be at least 50 $cm^2$ and that the total area of two electrodes used in defibrillation shall be at least 150 $cm^2$. The electrode member 21 has an area of at least 50 $cm^2$ and preferably about 80 $cm^2$ or more so that a pair of the electrodes used for defibrillation can be of the same size. 15 $cm^2$ is the minimum electrode area recommended for pediatric transthoracic use and the area of the electrode member 21 of the present invention for pediatric use can be made correspondingly smaller.

The carbon filled polymer electrode 21 is conductive in the plane of the electrode and transverse to the plane electrode and the silver/silver chloride coating on the under side of the electrode member is also conductive in the plane of the coating and transverse to the plane of the coating. The carbon filled polymer electrode member has a surface resistance substantially higher than the surface resistance of the silver/silver chloride coating and it has been found that the carbon filled polymer electrode member with the silver/silver chloride coating is not alone capable for transmitting and distributing the high levels of energy encountered in defibrillation over the entire surface of the electrode member. The current distributing mat 27 is configured to have electrical conductivity in the plane of the mat and transverse to the plane of the mat and a higher current carrying capacity than the sheet electrode member. The current distributing mat includes a non-woven open mesh metallized carbon fiber web having an electrically conductive carbon impregnated pressure sensitive adhesive composition on the upper and lower sides of the web. The web of the current distribution mat is thin and preferably less than five mills in thickness and is comprised of semi-metallic fibers such as carbon fibers which are metal plated or coated before or after being formed into a web with a metal coating that is 35% to 40% by weight of the metal plated carbon fiber web. The semi-metallic carbon fibers are X-ray transparent before plating or coating and the metal plating or coating of the fibers of the web is sufficiently thin, for example less than ten microns in thickness, and such that the thin open-mesh web formed of the metal plated fibers remains X-ray transparent. The electrically conductive pressure sensitive adhesive that is applied to opposite sides of the web is loaded with sufficient carbon or graphite for good electrical conductivity and such that the composite web and adhesive provide a mat that is electrically conductive in the plane of the mat and transverse to the plane of the mat. An example of a conductive double face pressure sensitive tape with a conductive carrier which can be used for the mat is a thin pressure sensitive bonding tape available from Adhesives Research, Inc., Glen Rock, Pa. under the trademark "Arclad", product No. 8001. This tape comprises a non-woven open mesh mat or carrier formed of metal coated carbon filaments having a metal coating of a few microns, for example five or six microns in thickness, and such that the metal coated mat is X-ray transparent. The electrically conductive pressure sensitive adhesive comprises a pressure sensitive adhesive impregnated with carbon or graphite for conductivity. U.S. Pat. No. 5,082,595 assigned to Adhesive Research, Inc. discloses a method of making such a double faced pressure sensitive adhesive tape with conductivity in X, Y and Z axes.

Published literature indicates that, when a metal plate electrode having an electrolytic gel coating on its underside, is placed on the skin and used to deliver current, the current density is very much higher under the perimeter of the electrode than under the center. A similar problem occurs at the energy accepting electrode of a set of such defibrillation electrodes. The mat 27 is arranged to distribute current over a central area of the electrode member 21 and has an outer perimeter 27p spaced inwardly of the perimeter 21p of the electrode member. The mat is sized to distribute the current more uniformly over the central portion of the electrode member to inhibit arcing through the central portion of the electrode member, and is spaced inwardly from the perimeter of the electrode member to avoid conveying high current levels to the outer periphery of the electrode member. For example, with an electrode member having an area of about 80 cm$^2$, a mat area of about 25 cm$^2$ has been found sufficient to distribute the energy of defibrillation pulses over a sufficiently large area to overcome arcing through the electrode member.

Figure 1:
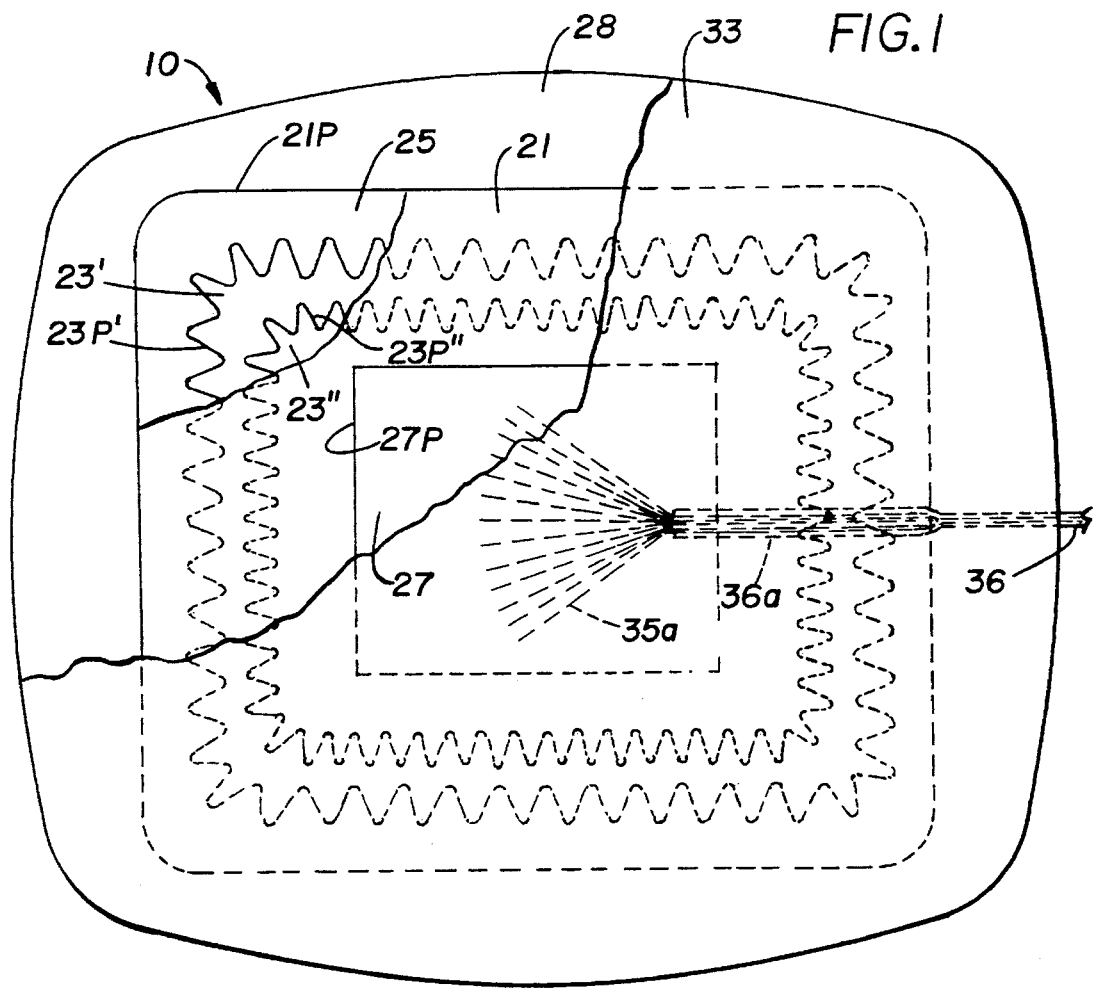
FIG. 1 is a top plan view of the electrode, with certain layers cut away to illustrate details of intermediate layers.

The silver/silver chloride coating can be applied to the entire under side of the electrode member. However, in order to reduce the possibility of skin irritation at the periphery of the electrode member, the outer perimeter of the silver/silver chloride coating 23 is preferably spaced inwardly from the perimeter 21p of the electrode member and outwardly of the perimeter 27p of the conductive mat. The silver/silver chloride coating is preferably formed in two layers each of a few microns in thickness with one layer designated 23' having an outer perimeter 23p' spaced inwardly of the perimeter 21p of the electrode member and a second layer 23" having an outer perimeter 23p" spaced inwardly from the perimeter 23p' and outwardly of the perimeter 27p of the current distributing mat 27. The layers 23', 23" are applied in successive layers on the electrode member 21 to allow a first layer to dry before applying the second. The layer 23" is preferably applied first with layer 23' underlying the layer 23". The dual layers provide higher electrical conductivity in the area where the silver/silver chloride layers overlap, with the conductivity stepping down in the single layer and decreasing to the conductivity of the carbon filled polymer of the electrode member 21 in the area outwardly of the silver/silver chloride coating. The area where the layers overlap, which corresponds to the area of coating 23', is preferably made substantially equal to the minimum active electrode area prescribed by ANSI/AAMI. For example, the layers 23' and 23" can each have a thickness of about 3 to 5 microns, with a combined thickness in the area of overlap of about six to ten microns. In addition, the outer perimeter of the layers 23' and 23" are advantageously serrated or undulated, for example as shown in FIGS. 1 and 3. This arrangement further decreases the current density by increasing the effective perimeter of the electrode member and minimizes the likelihood of skin burns or irritation.

In the embodiment of FIGS. 1–5, electrical conductors 35 are provided to conduct current to or from the electrode members. In some applications it is desirable that the conductors also be X-ray transparent. X-ray transparent conductors are preferably formed of metallized carbon fiber tows with an insulating sheath formed of an X-ray transparent material. The carbon fiber tows are preferably of a size having between 3,000 to 12,000 fibers and metal plated with a metal coating that is about 20% to 50% by weight of the metal plated carbon fiber tow. The higher weight plating on the larger size tows provides improved current carrying capacity for repeated defibrillation pulses. Standard carbon fiber tows are made from a polyacrylonitrile precursor and are referred to as pan base carbon fiber and are commercially available from Amoco Performance Products, Inc., Atlanta, Ga. In general, the carbon fiber tows are made by procedures described in U.S. Pat. No. 3,677,705 by heating polymeric fiber, e.g. acrylonitrile polymers or copolymers tin two stages, one to remove volatiles and carbonize and the other to convert amorphous carbon into crystal and carbon. During such procedures, the carbon changes from amorphous to single crystal and then orients into fibrous carbon. The fibrous carbon has a fiber diameter in the range of about 5 to 8 microns and the number of fibers in the tow can vary in a wide range from a few hundred to many thousand. The carbon fiber tows can be metal plated or coated by vacuum deposition for example as disclosed in U.S. Pat. No. 4,132,828; by vapor deposition for example as disclosed in U.S. Pat. No. 3,733,213; by electroplating such as disclosed in U.S. Pat. No. 4,661,403 or by chemical vapor deposition such as by thermo decomposition of nickel carbonyl gas.

In general, unplated pan base carbon fiber tows have a low density and are X-ray transparent as compared to metal wires of comparable size. Pan base carbon fiber tows have a longitudinal electrical resistance that is very high and longitudinal thermal conductivity that is very low as compared to metal wires of comparable size. Carbon fiber tows also exhibit anisotropic electrical conductivity which presents a problem when making electrical connection to other devices. The addition of the metal coating on the carbon fiber tows converts the conduction from anisotropic to isotropic, thereby alleviating the problem. Since the density of the carbon fiber tows is very low as compared to the density of the metal coating, a metal coating of 30% to 40% by weight of the metal plated carbon fiber tow is very thin and is X-ray transparent. The metal coating is preferably nickel which provides good electrical conductivity and corrosion resistance at moderate cost, but other metals such as copper or silver or gold could be used alone or in combination with the nickel coating.

The unsheathed end portion 35a of the conductor is spread or fanned out as shown in FIGS. 1 and 3 and pressed against the upper side of the conductive mat 27 to electrically connect the conductor to the mat and through the mat to the electrode member 21. In order to assure good conductivity and sealing of the fibers, the mat preferably includes a second section 27' arranged to overlie the unsheathed end portion of the conductor. Conveniently, the sections 27 and 27' of the mat can be formed in one piece and folded over so that they are interconnected at one end as shown in FIG. 5. In order to minimize the likelihood of pulling the conductors relative to the mat, the sheath 36 is preferably heat softened and flattened against the conductors 35 as by heated jaws 51 as shown in FIG. 4, prior to attachment of the conductor to the conductive mat. The sheath is preferably flattened over a length indicated at 36a sufficient to extend outwardly beyond the perimeter of the electrode 21 but inwardly of the perimeter of the cover, to minimize displacement of the gel pad. In electrode applications where X-ray transparency of the conductors is not required, the conductors can be formed of metal, preferably multi-strand conductors which can be spread out, to increase the contact area between the conductor and the conductive mat. When metal conductors are used, the electrode remains X-ray transparent, and only the metal wires and to a less extent the sheath, show up on the X-rays.

The electrode construction including the carbon filled polymer electrode member with the silver/silver chloride coating on the underside and the conductive mat having a metallized carbon fiber web and pressure sensitive adhesive on the upper and lower sides of the web, not only provides an electrode that is X-ray transparent and capable of transmitting energy at levels sufficient for defibrillation, but which also has a recovery time after delivery of a defibrillation pulse that meets or exceeds the AAMI/ANSI standards for pre-gelled ECG disposable electrodes. Thus, the electrodes can function as combination defibrillation electrodes and ECG electrodes. Since the electrodes are X-ray transparent, they can be positioned on the patient at any of the customary positions used for defibrillation without adversely affecting X-rays of the patient's chest in areas underlying the electrodes. As diagrammatically shown in FIG. 6, the energy delivering and energy accepting electrodes 10, 10' are connected through conductors 35, 35' to a polarized connector 50 to lead conductors 51, 51' connected to a combination defibrillator and ECG monitor 52. Further, electrodes configured in the manner described above are also capable of conducting AC energy at levels sufficient for use as current receiving or ground electrodes in electrosurgery.

The energy delivering and energy accepting electrodes 10 and 10' can also be used with defibrillation paddles. As shown in FIG. 7, an electrode 10" is configured the same as that previously described in connection with electrode 10, but the conductor 35 is omitted. The insulating cover sheet 33' is provided with an opening 33" in an area overlying the conductive mat, such that a defibrillation paddle can contact the mat. A removable cover sheet 36 is provided to cover the opening 33' prior to use of the electrode.

The electrode construction also provides more uniform current distribution over the electrode area than that achieved by prior electrodes using metal plates or metal wire mesh. The surface resistance (X, Y resistance) and the volume resistance (Z resistance) was measured using a pair of stainless steel blocks with the dimensions 1.0"×1.0"×0.5" and an ohmmeter. For measuring surface resistance the blocks were placed on the 3"×1" material with 1.0" between them. For measuring volume resistance, a piece of the layer or layers being tested was placed between the blocks so as to be sandwiched by them.

The surface resistance (X, Y resistance) of the conductive mat 27 is much lower than the surface resistance of the electrode member 21. The measured surface resistance of the electrode member (without any Ag/Agcl coat) was in a range of about 200 to 250 ohms/sq. in. for electrode members of about two mils in thickness and in a range of about 75 to 100 ohms/sq. in. for electrode members of about four mils in thickness, and the surface resistance varied in those ranges with the texture of the surface and the contact pressure between the blocks and the electrode member. The surface resistance of the conductive mat 27 was in a range of about 3 to 6 ohms/sq. in.

The surface resistance of the underside of the electrode member with the Ag/Agcl coating is lower than without the coating, and the surface resistance decreases as the thickness of the Ag/Agcl coating is increased. For example, the surface resistance of the electrode member having a single Ag/Agcl coating of about 3 to 4 microns, such as layer 23' is about 185 ohms/sq. in. and the electrode member having a thicker coating of about 9 or 10 microns has a surface resistance less than one ohm. The thickness of a coating in the area where the coatings 23' and 23" overlap, is preferably in the range of about 8 to 10 microns in thickness.

The resistance measured perpendicular to the surface is herein referred to the volume resistance or "Z" resistance. The volume resistance of the conductive mat 27 is about one or two ohms/sq. in. and the volume resistance of the other layers is lower, generally less than one ohm per square inch. The overall volume resistance of the electrode, measured from the top of conductive mat 27' to the underside center of Ag/Agcl coating 23' on the bottom of the electrode member, is only about one to three ohms/sq. in.

The DC resistance of the gel layer decreases rapidly with increasing current density and an ohmmeter cannot be used to indicate the resistance offered to defibrillation current. However, the volume or Z axis resistance of the gel is very low at the current density encountered in defibrillation.

The embodiments of the invention in which an exclusive property or privilege is claimed are defined as follows:

1. A disposable transcutaneous electrode comprising, a sheet electrode member of electrically conductive polymer having upper and lower sides and an outer perimeter, an electrically conductive silver/silver chloride coating on at least a major portion of the lower side of the electrode member, a pad of electrically conductive gel having an upper surface underlying the silver/silver chloride coating on the lower side of the electrode member, a removable carrier sheet on a lower surface of the pad for covering the latter prior to use, a current distributing mat having upper and lower surfaces and an outer perimeter spaced inwardly of the outer perimeter of the electrode member, the mat including an open mesh metallized carbon fiber web having a carbon impregnated pressure sensitive adhesive composition on upper and lower sides of the web, the mat being configured to be electrically conductive along the surfaces of the mat and transverse to the surfaces of the mat, the mat having the lower surface conductively adhered to the upper side of the sheet electrode member, means for conducting defibrillating energy to or from the upper side of the mat and a medical device, the sheet electrode member and the current distributing mat being configured to be X-ray transparent and capable of conducting energy at levels sufficient for defibrillation.

2. An electrode according to claim 1 wherein the means for conducting defibrillation energy comprises an electrical conductor sheathed in an electrical insulating material and having an unsheathed end portion conductively adhered to the mat.

3. An electrode according to claim 1 wherein the electrical resistance of the mat in directions paralleling the surface of the mat is less than the electrical resistance of the sheet electrode member in directions paralleling the upper side of the sheet electrode member.

4. An electrode according to claim 1 wherein the silver/silver chloride coating has an outer edge spaced inwardly of the outer perimeter of the sheet electrode member.

5. An electrode according to claim 1 wherein the silver/silver chloride coating includes first and second layers, the first layer having an outer edge spaced inwardly of the outer perimeter of the sheet electrode member and the second layer having an outer edge spaced inwardly of the outer edge of the first layer.

6. A disposable transcutaneous electrode comprising, a sheet electrode member of electrically conductive carbon filled polymer having upper and lower sides and an outer perimeter, an electrically conductive silver/silver chloride coating on at least a major portion of the lower side of the electrode member, a pad of electrically conductive gel having an upper surface underlying the silver/silver chloride coating on the lower side of the electrode member, a removable carrier sheet on a lower surface of the pad for covering the latter prior to use, a current distributing mat having upper and lower surfaces and an outer perimeter spaced inwardly of the outer perimeter of the electrode member, the mat including an open mesh metallized carbon fiber web having a carbon impregnated pressure sensitive adhesive composition on upper and lower sides of the web, the mat being configured to be electrical conductive along the surfaces of the mat and transverse to the surfaces of the mat, the mat having the lower surface conductively adhered to the upper side of the sheet electrode member, an electrical conductor sheathed in an electrical insulating material and having an unsheathed end portion conductively adhered to the mat for conducting defibrillating energy to or from the upper side of the mat and a medical device, the sheet electrode member and the current distributing mat being configured to be X-ray transparent and capable of conducting energy sufficient for defibrillation.

7. An electrode according to claim 6 including a second mat having a metallized carbon fiber web and electrically conductive pressure sensitive adhesive composition on upper and lower sides, the end portion of the conductor being adhered to the upper side of the first-mentioned mat and the lower side of the second mat overlying and adhered to the end portion of the conductor and at least a portion of the upper side of the first-mentioned mat.

8. An electrode according to claim 7 wherein said conductor comprises an X-ray transparent metal coated carbon fiber tow.

9. An electrode according to claim 8 wherein the metal coating on the carbon fiber tow is about 20% to 50% by weight of the metal coated carbon fiber tow.

10. An electrode according to claim 8 wherein tow of carbon fibers has greater than six thousand fibers.

11. An electrode according to claim 6 wherein said conductor comprises an X-ray transparent nickel plated carbon fiber tow.

12. An electrode according to claim 6 wherein said conductor comprises a multiple strand metallic conductor.

13. An electrode according to claim 6 wherein the sheath is formed of a thermoplastic material and the sheath is best softened and flattened to a thickness less than the normal thickness of the sheath along a length contiguous to the unsheathed end portion.

14. A set of disposable transcutaneous electrodes including an energy delivering electrode and an energy accepting electrode, each electrode comprising, a sheet electrode member of electrically conductive carbon filled polymer having upper and lower sides and an outer perimeter, an electrically conductive silver/silver chloride coating on at least a major portion of the lower side of the electrode member, a pad of electrically conductive gel having an upper surface underlying the silver/silver chloride coating on the lower side of the electrode member, a removable carrier sheet on a lower surface of the pad for covering the latter prior to use, a current distributing mat having upper and lower surfaces and an outer perimeter spaced inwardly of the outer perimeter of the electrode member, the mat including an open mesh metallized carbon fiber web having a carbon impregnated pressure sensitive adhesive composition on upper and lower sides of the web, the mat being configured to be electrical conductive along the surfaces of the mat and transverse to the surfaces of the mat, the mat having the lower surface conductively adhered to the upper side of the sheet electrode member, an electrical conductor sheathed in an electrical insulating material and having an unsheathed end portion conductively adhered to the mat for conducting defibrillating energy to or from the upper side of the mat and a medical device, the sheet electrode member and the current distributing mat being configured to be X-ray transparent and capable of conducting energy sufficient for defibrillation, and a cover member of electrical insulating material attached to the upper sheet electrode and mat.

15. An electrode set according to claim 14 wherein each electrode includes a second mat having a metallized carbon fiber web and electrical resistance of the mat in directions paralleling the surface of the mat is less than the electrical resistance of the sheet electrode member in directions paralleling the upper side of the sheet electrode member.

16. An electrode set according to claim 14 wherein the silver/silver chloride coating on each electrode has an outer edge spaced inwardly of the outer perimeter of the sheet electrode member.

17. An electrode set according to claim 14 wherein the silver/silver chloride coating on each electrode includes first and second layers, the first layer having an outer edge spaced inwardly of the outer perimeter of the sheet electrode member and the second layer having an outer edge spaced inwardly of the outer edge of the first layer.

18. An electrode set according to claim 14 wherein the electrical conductor associated with each electrode comprises an X-ray transparent metal coated carbon fiber tow.

19. An electrode set according to claim 18 wherein the metal coating on the carbon fiber tow is at least 30% by weight of the metal coated carbon fiber tow.

20. An electrode set according to claim 19 wherein tow of carbon fibers has greater than six thousand fibers.

21. An electrode set according to claim 14 wherein the electrical conductor associated with each electrode comprises an X-ray transparent nickel plated carbon fiber tow.

22. An electrode set according to claim 14 wherein the electrical conductor associated with each electrode comprises a multiple strand metallic conductor.

23. A disposable transcutaneous energy accepting electrode comprising, a sheet electrode member of electrically conductive carbon filled polymer having upper and lower sides and an outer perimeter, an electrically conductive silver/silver chloride coating on at least a major portion of the lower side of the electrode member, a pad of electrically conductive gel having an upper surface underlying the silver/silver chloride coating on the lower side of the electrode member, a removable carrier sheet on a lower surface of the pad for covering the latter prior to use, a current distributing mat having upper and lower surfaces and an outer perimeter spaced inwardly of the outer perimeter of the electrode member, the mat including an open mesh metallized carbon fiber web having a carbon impregnated pressure sensitive adhesive composition on upper and lower sides of the web, the mat being configured to be electrical conductive along the surfaces of the mat and transverse to the surfaces of the mat, the mat having the lower surface conductively adhered to the upper side of the sheet electrode member, an electrical conductor sheathed in an electrical insulating material and having an unsheathed end portion conductively adhered to the mat for conducting defibrillating energy to or from the upper side of the mat, the sheet electrode member and the current distributing mat being configured to be X-ray transparent and capable of conducting energy at levels sufficient for use as an energy receiving electrode in defibrillation and electro-surgery.

24. A disposable transcutaneous electrode comprising, a sheet electrode member of electrically conductive polymer having upper and lower sides and an outer perimeter, an electrically conductive metallic layer conductively affixed to at least a major portion of the lower side of the electrode member, the electrode member having a surface electrical resistance, measured in directions paralleling the upper and lower sides, higher than the surface electrical resistance of the metallic layer, a pad of electrically conductive gel having an upper surface underlying the metallic layer on the lower side of the electrode member, a current distributing mat having upper and lower surfaces and an outer perimeter spaced inwardly of the outer perimeter of the electrode member, the mat being configured to be electrically conductive along the surfaces of the mat and transverse to the surfaces of the mat, the mat having surface electrical resistance, measured in directions paralleling the surfaces of the mat, less than the surface electrical resistance of the sheet electrode member, the mat having the lower surface conductively affixed to the upper side of the sheet electrode member, and means for conducting defibrillating energy to or from the mat and a medical device, the sheet electrode member and the current distributing mat being configured to be capable of conducting energy at levels sufficient for defibrillation.

25. A disposable transcutaneous electrode comprising, a sheet electrode member of electrically conductive carbon filled polymer material having upper and lower sides and an outer perimeter, an electrically conductive metal/metal chloride coating on at least a major portion of the lower side of the electrode member, a pad of electrically conductive gel having an upper surface underlying the metal/metal chloride coating on the lower side of the electrode member, a current distributing mat having upper and lower surfaces and an outer perimeter spaced inwardly of the outer perimeter of the sheet electrode member, the mat including a metallized carbon fiber web having a carbon impregnated electrically conductive pressure sensitive adhesive composition on upper and lower sides of the web, the mat being configured to be electrically conductive along the surfaces of the mat and transverse to the surfaces of the mat, the mat having surface electrical resistance, measured in directions paralleling the surfaces of the mat, less than the surface electrical resistance of the sheet electrode member measured in directions paralleling the sides of the sheet electrode member, the mat having the lower surface conductively adhered to the upper side of the sheet electrode member, an electrical conductor sheathed in an electrical insulating material and having an unsheathed end portion conductively adhered to the mat for conducting defibrillating energy to or from the upper side of the mat and a medical device, the sheet electrode member and the current distributing mat being configured to be x-ray translucent and capable of conducting energy sufficient for defibrillation.

\* \* \* \* \*